US010471257B2

United States Patent
Ahmad et al.

(10) Patent No.: US 10,471,257 B2
(45) Date of Patent: Nov. 12, 2019

(54) IMPLANTABLE TEMPORARY NERVE CONDUCTION BLOCKING METHOD AND SYSTEM

(71) Applicant: THE CLEVELAND CLINIC FOUNDATION, Cleveland, OH (US)

(72) Inventors: Usman Ahmad, Cleveland, OH (US); Sudish Murthy, Cleveland Heights, OH (US); Jonathan Sakai, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 2 days.

(21) Appl. No.: 15/596,030

(22) Filed: May 16, 2017

(65) Prior Publication Data
US 2017/0333714 A1 Nov. 23, 2017

Related U.S. Application Data (60) Provisional application No. 62/338,648, filed on May 19, 2016.

(51) Int. Cl.
*A61N 1/00* (2006.01)
*A61N 1/36* (2006.01)
(Continued)

(52) U.S. Cl.
CPC ....... *A61N 1/36071* (2013.01); *A61N 1/0456* (2013.01); *A61N 1/0504* (2013.01);
(Continued)

(58) Field of Classification Search
CPC ................ A61N 1/36071; A61N 2/008; A61N 1/36021; A61N 1/36017; A61N 1/06;
(Continued)

(56) References Cited

U.S. PATENT DOCUMENTS 8,626,302 B2  1/2014  Bennett et al.
8,700,177 B2  4/2014  Strother et al.
(Continued)

FOREIGN PATENT DOCUMENTS

WO  2006084635 A2  8/2006
WO  2006135751 A2  12/2006
WO  2015196164 A2  12/2015

OTHER PUBLICATIONS

International Search Report corresponding to International Patent Application No. PCT/US2017/032786, dated Jul. 7, 2017, pp. 1-11.
(Continued)

*Primary Examiner* — Scott M. Getzow
(74) *Attorney, Agent, or Firm* — Tarolli, Sundheim, Covell & Tummino LLP (57) ABSTRACT

Systems and methods of reducing pain after surgery in the thoracic or abdominal region and managing chronic nerve pain in the thoracic or abdominal region are provided. Such methods involve an electrode assembly that has a proximal portion and a distal portion with the distal portion including a plurality of electrodes. At least one electrode of the plurality of electrodes is placed over each of a plurality of intercostal nerve bundles in the patient's body. The proximal portion of the electrode assembly is connected to a pulse generator. An electromagnetic field is applied to the plurality of intercostal nerve bundles. The plurality of electrodes is removed from the patient's body after an intercostal nerve block sufficient to alleviate the patient's pain has been achieved.

19 Claims, 11 Drawing Sheets

(51) Int. Cl.
*A61N 1/05* (2006.01)
*A61N 1/06* (2006.01)
*A61N 1/04* (2006.01)
*A61N 2/00* (2006.01)

(52) U.S. Cl.
CPC ......... *A61N 1/0551* (2013.01); *A61N 1/0553* (2013.01); *A61N 1/06* (2013.01); *A61N 1/36017* (2013.01); *A61N 1/36021* (2013.01); *A61N 2/008* (2013.01); *A61N 1/0476* (2013.01); *A61N 1/0558* (2013.01)

(58) Field of Classification Search
CPC .. A61N 1/0456; A61N 1/0553; A61N 1/0551; A61N 1/0504; A61N 1/0476; A61N 1/0558

See application file for complete search history.

(56) References Cited

U.S. PATENT DOCUMENTS

| | | | |
|---|---|---|---|
| 8,788,046 B2 | 7/2014 | Bennett et al. | |
| 8,788,047 B2 | 7/2014 | Bennett et al. | |
| 8,788,048 B2 | 7/2014 | Bennett et al. | |
| 8,805,533 B2 | 8/2014 | Boggs, II et al. | |
| 8,886,337 B2 | 11/2014 | Bennett et al. | |
| 8,965,516 B2 | 2/2015 | Bennett et al. | |
| 9,248,289 B2 | 2/2016 | Bennett et al. | |
| 2004/0049231 A1* | 3/2004 | Hafer ................ A61B 17/3401 607/3 |
| 2013/0238066 A1 | 9/2013 | Boggs, II et al. | |

OTHER PUBLICATIONS

Johnson et al.,(2010). "Implantation of an intercostal nerve stimulator for chronic abdominal pain," The Royal College of Surgeons of England. pp. 1-3.

Solak et al., (2016). "Transcutaneous Electric Nerve Stimulation for the Treatment of Postthoracotomy Pain: A Randomized Prospective Study." The Thoracic and cardiovascular surgeon. Apr. 2007. pp. 1-5.

Graybill et al., (2011). "Spinal Cord Stimulation for Treatment of Pain in a Patient with Post Thoracotomy Pain Syndrom." Pain Physician 2011. pp. 1-6.

\* cited by examiner

IMPLANTABLE TEMPORARY NERVE CONDUCTION BLOCKING METHOD AND SYSTEM

RELATED APPLICATION

This application claims priority from U.S. Provisional Application No. 62/338,648, filed 19 May 2016, the subject matter of which is incorporated herein by reference in its entirety.

TECHNICAL BACKGROUND

The present disclosure relates to systems and methods for temporarily blocking peripheral nerve conduction to alleviate pain in a patient suffering therefrom.

BACKGROUND

Pain after thoracic, cardiac or abdominal surgery can be severe and contribute to peri-operative morbidity and mortality in the acute phase. Such acute pain may not decrease substantially over the course of hospitalization and the first postoperative month. Chronic pain can last for months to years. Other than pain syndromes associated with limb amputation, pain after thoracic surgery is one of the most recognized pain syndrome associated with a specific surgery. Post-operative pain is significantly associated with poor respiratory effort, mobility and a higher risk of ensuing complications such as pneumonia, atelectasis, and deep vein thrombosis.

Current methods of controlling post-operative pain after such surgeries include administering narcotics and other traditional pharmacologic agents. However, such systemic medications often have side effects not tolerated by patients. Further, such medications are often delivered by invasive epidural, spinal or paravertebral procedures. As such, a need exists for a less invasive and targeted treatment for post-operative pain after surgeries involving the thoracic and abdominal region.

SUMMARY

The present disclosure relates to temporarily blocking peripheral nerve conduction to alleviate pain in a patient suffering therefrom.

In certain embodiments, a method is provided to alleviate pain in a patient after surgery in the abdominal or thoracic region by blocking nerve conduction in intercostal nerve bundles. The method comprises obtaining an electrode assembly having a proximal portion and a distal portion. The distal portion comprises a plurality of electrodes. The method further includes placing an electrode of the plurality of electrodes over each of a plurality of intercostal nerve bundles of the patient's body. The proximal portion of the electrode assembly is connected to a pulse generator. The method further includes applying an electromagnetic field to the plurality of intercostal nerve bundles after the patient's surgery. The plurality of electrodes can be percutaneously removed from the patient's body after achieving an intercostal nerve block to alleviate the patient's pain.

In certain embodiments, the electrode assembly comprises a plurality of electrical nodes and an electrical wire electrically coupled to the plurality of electrical nodes. The method includes placing an electrical node of the plurality of electrical nodes over each of a plurality of intercostal nerve bundles of the patient's body inside the pleural space. The method further includes connecting a proximal portion of the electrical wire to a pulse generator. An electromagnetic field is applied to the plurality of intercostal nerve bundles after the surgery. The plurality of electrical nodes can be percutaneously removed after achieving an intercostal nerve block sufficient to alleviate the patient's pain.

In certain embodiments, the electrode assembly is an electrical lead comprising a lead body having a proximal portion and a distal portion. The distal portion comprises a plurality of electrodes. The method includes placing an electrode of the plurality of electrodes over each of a plurality of intercostal nerve bundles of the patient's body. The method further includes connecting the proximal portion of the lead to a pulse generator. An electromagnetic field is applied to the plurality of intercostal nerve bundles after the surgery. The plurality of electrodes can be percutaneously removed from the patient's body after achieving an intercostal nerve block sufficient to alleviate the patient's pain.

In certain embodiments an electrode assembly system is provided. The electrode assembly system comprises an electrical lead, a sheath, and a tunneler. The sheath has a lumen extending therethrough that is sized and configured to accommodate both the electrical lead and the tunneler. In particular, the electrical lead comprises a lead body having a proximal portion and a distal portion. The distal portion comprises a plurality of un-insulated electrically conductive sections and a plurality of opposing insulated sections. A plurality of flexible stabilizing tines laterally extends from the distal portion of the lead body. The sheath comprises a sheath body having a proximal end, a distal end, and a lumen extending therebetween. The sheath body has a cross-sectional configuration that accommodates the plurality of stabilizing tines of the electrical lead. Preferably, the proximal end of the sheath body has an alignment fin. The tunneler comprises a tunneler body having a proximal end and a distal end. At least a portion of the tunneler is configured to be disposed within the sheath. Preferably, the proximal end of the tunneler comprises an alignment handle and the distal end has a tapered configuration.

In certain embodiments, the present disclosure provides a method of using an electrode assembly system to deliver an intercostal nerve block subcutaneously to alleviate pain in a patient after surgery in the abdominal or thoracic region. The method comprises obtaining an electrode assembly system comprising an electrical lead, a sheath and a tunneler as described above. The method further comprises inserting through an incision in the patient's skin the sheath with the tunneler disposed therein. The method also includes positioning the sheath subcutaneously over a plurality of intercostal nerve bundles. The sheath can be positioned substantially perpendicular to the patient's ribs or intercostal nerve bundles or substantially parallel to the patient's ribs or intercostal nerve bundles. The method includes withdrawing the tunneler and inserting the distal portion of the electrical lead into the sheath. The distal portion of the electrical lead is oriented such that the plurality of un-insulated electrically conductive sections is facing towards the plurality of intercostal nerve bundles and away from the cutaneous fibers of the patient's body. The sheath is then removed and the proximal portion of the electrical lead is connected to a pulse generator. An electromagnetic field is applied to the plurality of intercostal nerve bundles. The method then comprises withdrawing the distal portion of the lead after achieving an intercostal nerve block sufficient to alleviate the patient's pain.

DETAILED DESCRIPTION

The disclosure herein refers to the term "substantially" with respect to certain geometric configurations and orientations. By "substantially" is meant that the configuration or orientation of the element need not have the mathematically exact described configuration or orientation but can have a configuration or orientation that is recognizable by one skilled in the art as generally or approximately having the described configuration or orientation. The disclosure also refers to the term "perpendicular" and "parallel." These terms are used with reference to the anatomical orientation of a human patient in a standard anatomical position as is known in the art.

Further, as used herein with respect to a described element, the terms "a," "an," and "the" include at least one or more of the described element unless otherwise indicated. Further, the term "or" refers to "and/or" unless otherwise indicated. In addition, it will be understood that when an element is referred to as being "over," "on," "attached" to, "connected" to, "coupled" to etc., another element, it can be directly over, on, attached to, connected to, coupled to, etc. the other element or intervening elements may also be present. In contrast, when an element is referred to as being, for example, "directly over," "directly on," "directly attached" to, "directly connected" to or "directly coupled" to another element, there are no intervening elements present.

The present disclosure provides methods and devices for delivering an intercostal nerve block to alleviate pain in a patient suffering therefrom. The intercostal nerve bundles are part of the somatic nervous system and arise from the anterior rami of the thoracic spinal nerves from T1 to T11. Because intercostal nerve bundles arise from the somatic nervous system, this enables them to control the contraction of muscles, as well as provide specific sensory information regarding the skin and parietal pleura. Intercostal nerves connect to the appropriate ganglion in the sympathetic trunk through rami communicantes and serve the thoracic pleura and the abdominal peritoneum.

Figure 1:
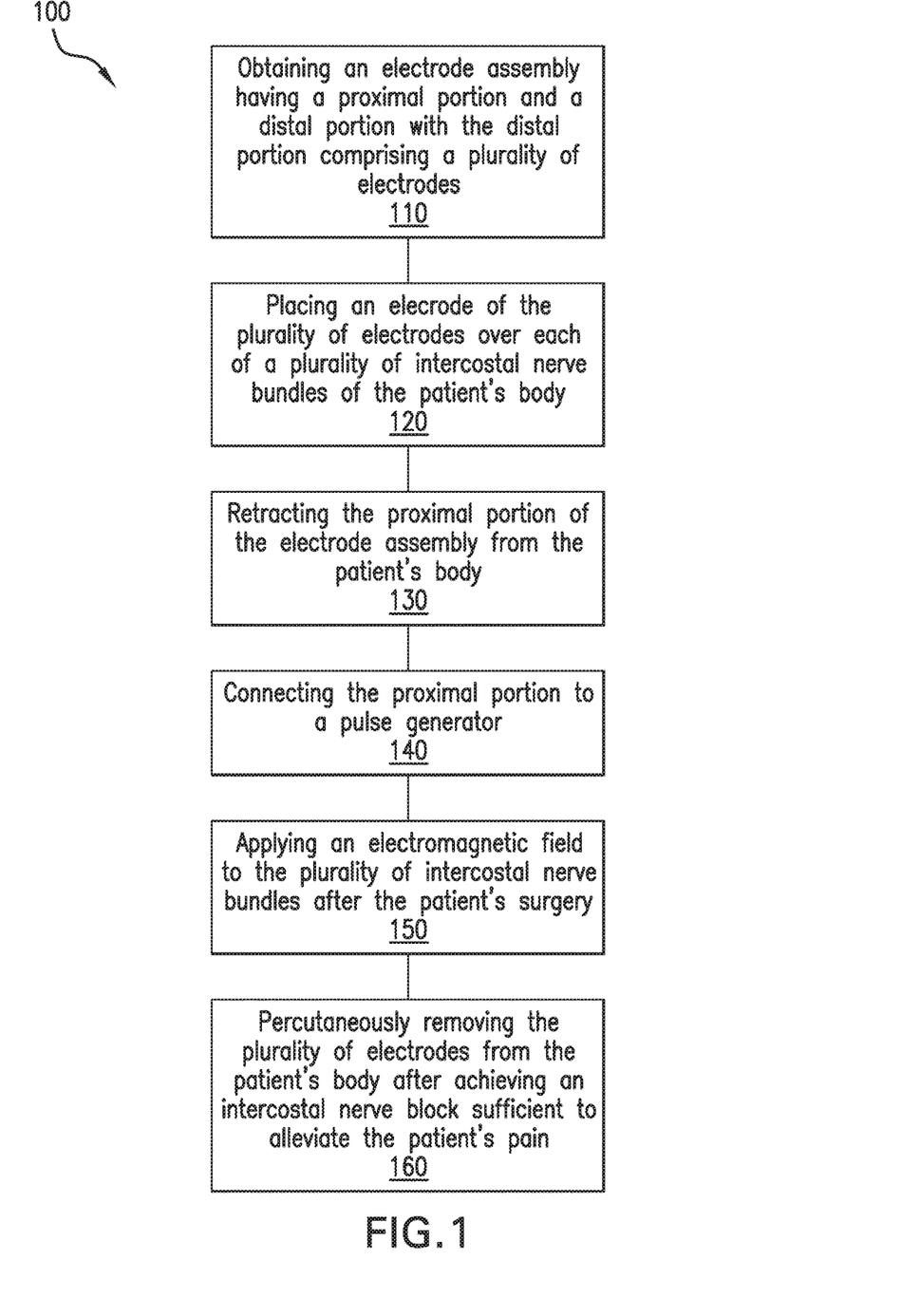
FIG. 1 is a flow chart depicting exemplary steps of a method of an embodiment of the present disclosure.

In certain embodiments, intercostal nerve conduction is blocked in a patient who has undergone surgery in the abdominal or thoracic region. Methods involve macro-stimulation of intercostal nerve bundles as opposed to micro-stimulation of individual specific fibers within these nerve bundles. With reference to the flowchart of FIG. 1, a method 100 of providing an intercostal nerve block to alleviate pain in a patient after surgery in the abdominal or thoracic region involves obtaining an electrode assembly having a proximal portion and a distal portion 110. The distal portion comprises a plurality of electrodes. The method further includes placing an electrode of the plurality of electrodes over each of a plurality of intercostal nerve bundles of the patient's body 120. In certain embodiments, the plurality of electrodes is placed substantially parallel to the intercostals nerve bundles of the patient's body. In other embodiments, the plurality of electrodes is placed substantially perpendicular to the intercostal nerve bundles of the patient's body. The method further includes connecting the proximal portion to a pulse generator 140. In certain embodiments, the method includes retracting the proximal portion of the electrode assembly from the patient's body 130 and then connecting the proximal portion to a pulse generator 140. An electromagnetic field is applied to the plurality of intercostal nerve bundles after the patient's surgery 150. The method then includes percutaneously removing the plurality of electrodes from the patient's body after achieving an intercostal nerve block sufficient to alleviate the patient's pain 160. The intercostal nerve block can be a complete nerve block or a partial nerve block so long as the patient's pain has been alleviated.

The electrode assembly can have various different configurations as described in more detail below. For example, with reference to the schematic illustration of the thoracic cavity depicted in FIG. 2, a method of the present disclosure comprises obtaining an electrode assembly 13 that is an electrical lead 10. Electrical lead 10 comprises a lead body 11 that has a proximal portion 12 and a distal portion 14. Distal portion 14 comprises a plurality of electrodes 16. Although not expressly depicted in FIG. 2, if a single electrical lead is used, such an electrical lead generally has a plurality of electrodes at a distal portion thereof, a plurality of electrical contacts at a proximal portion thereof, and a conductor extending between and electrically coupled to the plurality of electrodes and the plurality of electrical contacts. The conductor can be a straight wire or a helically coiled conductor. The plurality of electrical contacts is configured to electrically couple to a pulse generator.

Referring again to FIG. 2, an electrode 16 of the plurality of electrodes is placed over each of a plurality of intercostal nerve bundles 20 of the patient's body. In other words, one or more electrodes are placed at multiple levels (any suitable levels between T1-T11) of intercostal nerve bundles. The electrodes need not be placed over intercostal nerve bundles at every thoracic spinal level so long as the electrodes are placed over more than one intercostal nerve bundle. The electrodes are preferably placed as close to the intercostal nerve bundles as possible and can be fixated to adjacent tissue, such as intercostal muscles, via various fixation devices such as sutures or clips, for example. Preferably, the electrodes are placed proximal to the chest incision but sufficiently away from the sympathetic nerve chain so as to not activate the sympathetic nerve chain. Proximal portion 12 is connected to pulse generator 22. In certain embodiments, proximal portion 12 is percutaneously retracted from the patient's body and connected to pulse generator 22. An electromagnetic field is then applied via pulse generator 22 to the plurality of intercostal nerve bundles 20 after the surgery. Distal portion 14 of electrical lead 10 can then be percutaneously removed from the patient's body after achieving an intercostal nerve block sufficient to alleviate the patient's pain. As such, when the patient no longer requires application of the electromagnetic field, the distal portion of the electrical lead can be removed just like a chest tube. Accordingly, such a method provides a removable system and does not require an extra invasive procedure (such as epidural/spinal/paravertebral placement).

Figure 3:
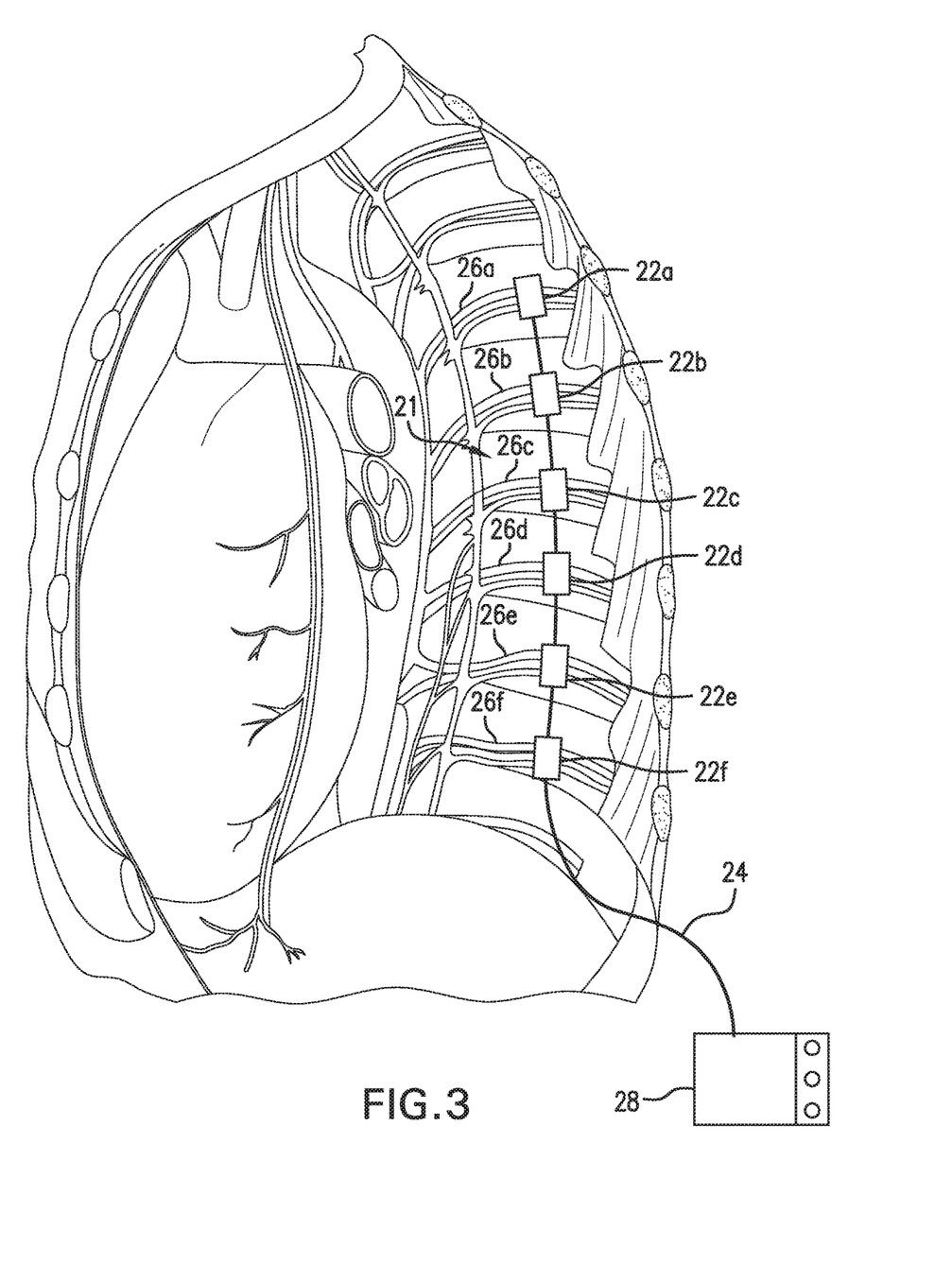
FIG. 3 is a schematic illustration of a thoracic cavity with another embodiment of an electrode assembly positioned over a plurality of intercostal nerve bundles.

In other embodiments of the present disclosure, the electrode assembly comprises single individual electrical nodes as depicted in FIG. 3. In particular, electrode assembly 21 comprises a plurality of electrical nodes 22 and an electrical wire 24 electrically coupled to the plurality of electrical nodes 22. An electrical node 22 of the plurality of electrical nodes is placed over each of a plurality of intercostal nerve bundles 26 of the patient's body. A proximal portion of electrical wire 24 is connected to a pulse generator 28. In certain embodiments, the proximal portion of electrical wire 24 is percutaneously retracted from the patient's body and connected to pulse generator 28. An electromagnetic field is applied to the plurality of intercostal nerve bundles 26 after the surgery. The plurality of electrical nodes 22 is percutaneously removed after an intercostal nerve block has been achieved sufficient to alleviate the patient's pain.

Figure 4:
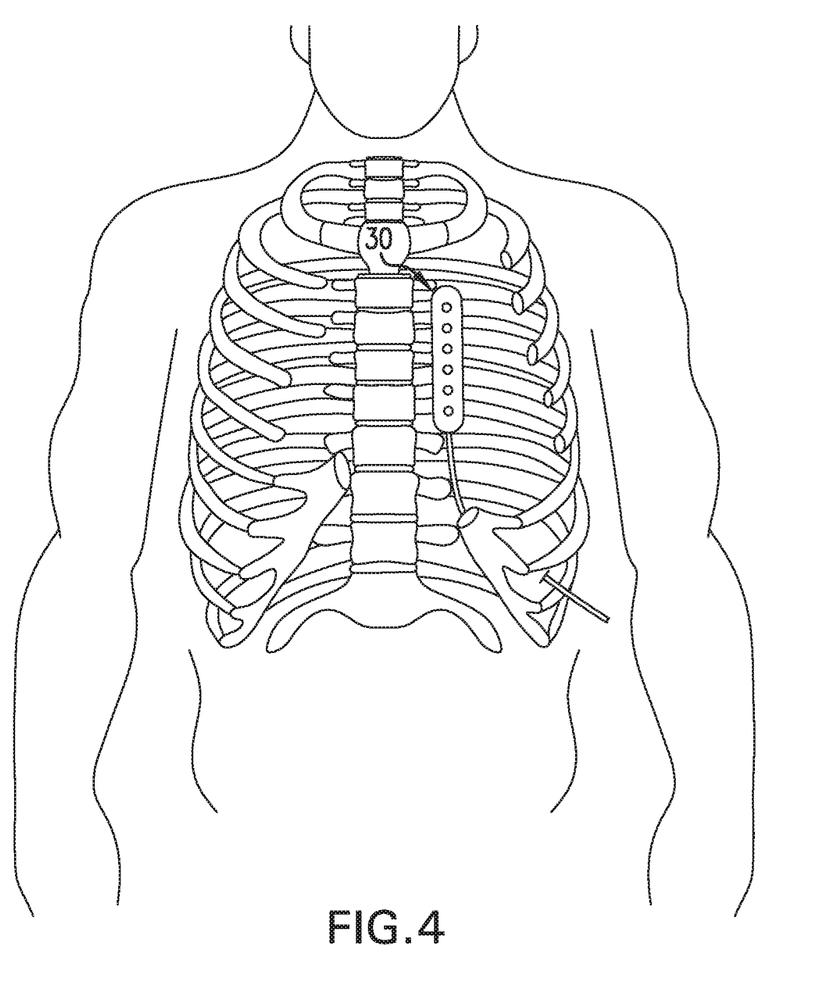
FIG. 4 is a schematic illustration of a thoracic cavity with another embodiment of an electrode assembly positioned over a plurality of intercostal nerve bundles.
Figure 4A:
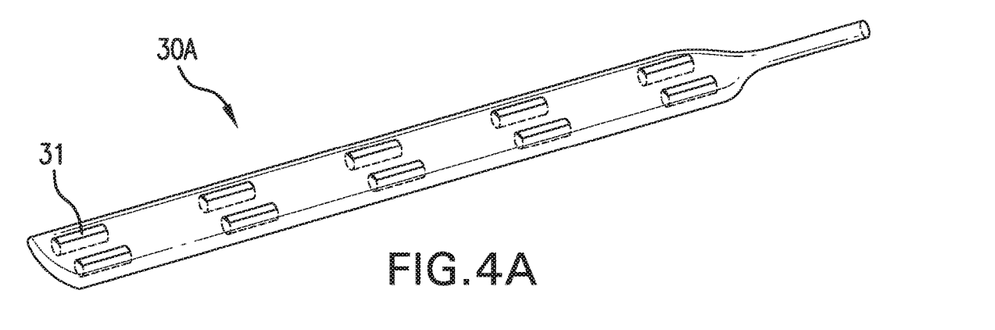
FIG. 4A is a perspective view of an embodiment of an electrode assembly according to an embodiment of the present disclosure
Figure 4B:
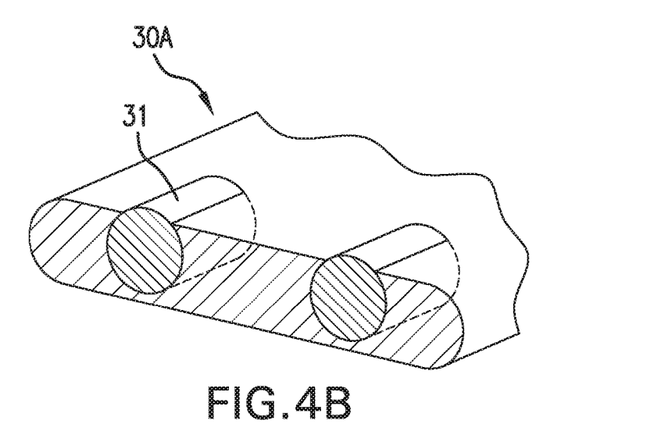
FIG. 4B is a cross-sectional view of the electrode assembly depicted in FIG. 4A.

As mentioned above, the electrode assembly can have different configurations so long as at least one electrode of the electrode assembly can be placed on each of a plurality of intercostal nerve bundles such that intercostal nerve bundles are blocked at multiple spinal levels. For example, the electrode assembly can be a paddle-style lead 30 as shown in FIG. 4. The electrodes can be flat as illustrated in FIG. 4 or can be cylindrical as illustrated in FIG. 4A. As illustrated in FIG. 4B, electrodes 31 on a paddle-style lead 30A can be cylindrical electrodes that are partially embedded in the paddle mold for strength. In certain embodiments, the lead has a diameter of between about 3 mm to about 6 mm. In certain embodiments, the lead has a diameter of about 2.7 mm. Preferably the paddle-style lead is thick enough to retain itself like a chest tube without anchoring. In certain embodiments, the paddle-style lead has a length of about 150 mm, a width of about 10 mm and a thickness of about 3 mm. As illustrated in FIGS. 4A and 4B, the electrodes can be arranged as a two-column array of electrodes such that paired electrodes run substantially parallel to the nerve bundles.

Figure 5:
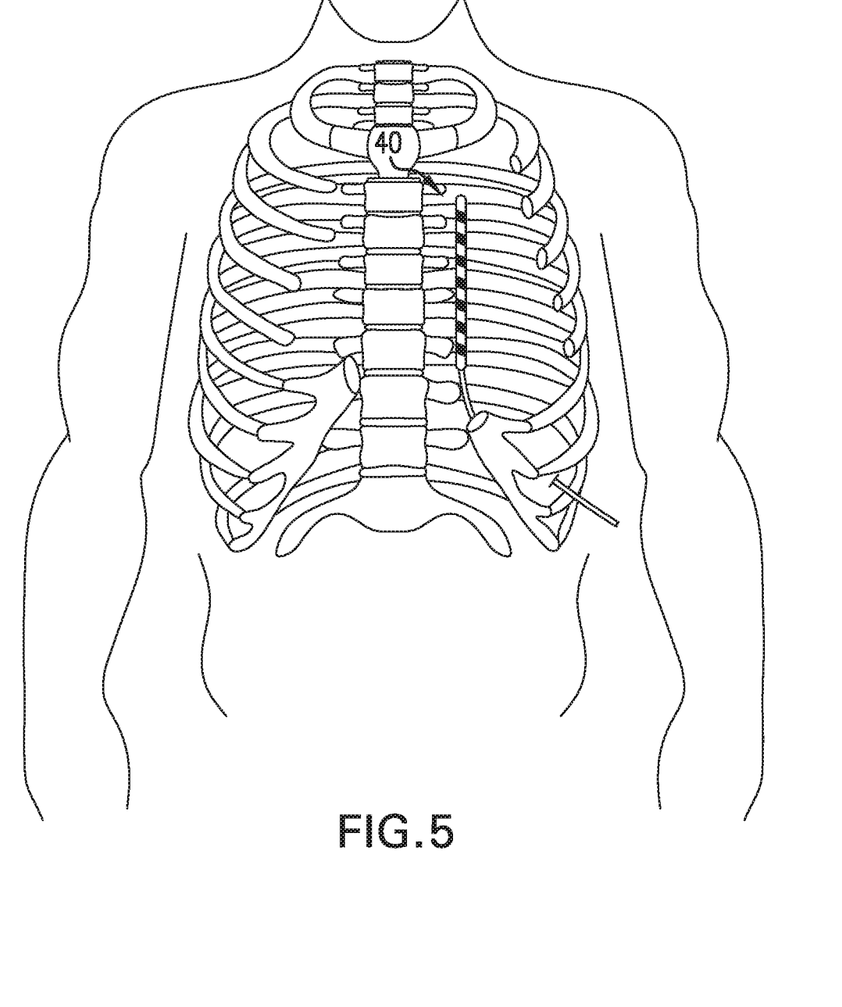
FIG. 5 is a schematic illustration of a thoracic cavity with another embodiment of an electrode assembly positioned over a plurality of intercostal nerve bundles.
Figure 5A:
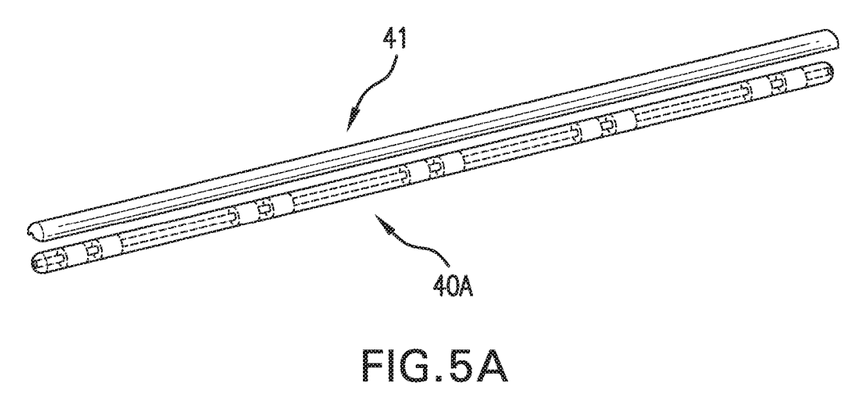
FIG. 5A is an exploded view of another embodiment of an electrode assembly according to the present disclosure.
Figure 6:
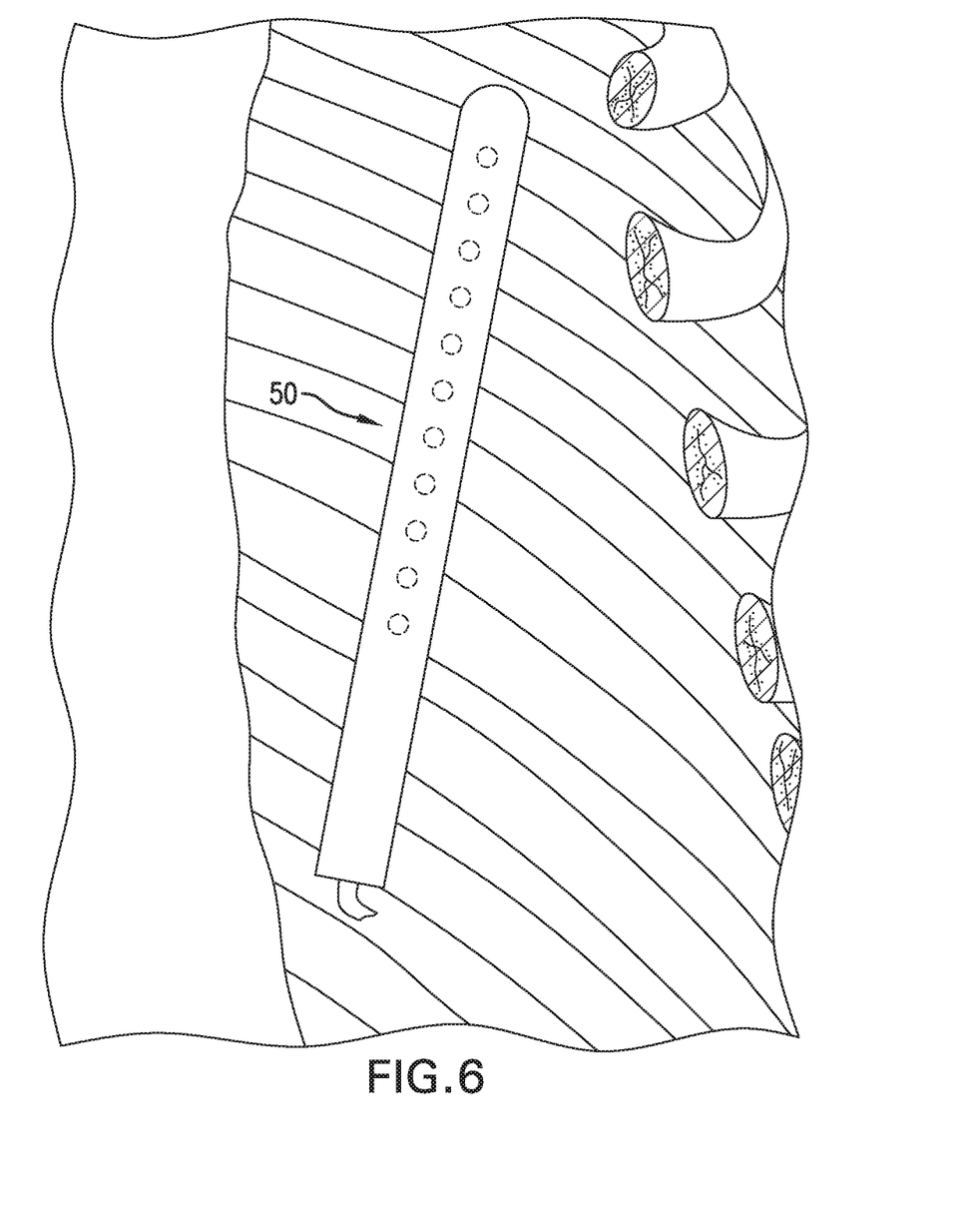
FIG. 6 is a schematic illustration of a thoracic cavity with another embodiment of an electrode assembly positioned over a plurality of intercostal nerve bundles.

Alternatively, the electrode assembly can be a cylindrical lead 40 as shown in FIG. 5. The electrode assembly can also be incorporated into/built into a chest tube or can be incorporated into a sleeve non-slidably or slidably attached over a chest tube. As shown in FIG. 5A, a cylindrical lead 40A can include an insulated cover 41 that is snapped or overmolded onto one side of the lead 40A to shield the non-stimulation surface from receipt of current. Cover 41 can be a separate component that is placed on the non-stimulation surface intra-operatively. The electrode assembly can also be a strip electrode 50 as illustrated in FIG. 6. As seen in these figures, the orientation of the electrode assemblies is such that the electrodes are facing intercostals nerves. The cylindrical lead 40 or strip electrode 50 can contain a number of electrode contacts that exceeds the number of intercostal nerves to be activated such that the contacts can be selectively programmed by the pulse generator so as to minimize the distance between electrode pairs (for bipolar stimulation) or single electrodes (for monopolar stimulation) between the electromagnetic field and the target nerve. The electrode assemblies can be selectively insulated such that the distal portion of the electrode assembly has un-insulated electrically conductive sections and opposing insulated sections (i.e. on opposite sides of the electrode assembly). When placed over the intercostal nerve bundles, the un-insulated electrically conductive sections can be oriented such that they are facing towards the plurality of intercostal nerve bundles. To that end, in certain embodiments, the opposing insulated sections are oriented such that they face towards the cutaneous fibers. The electrode assemblies can also include radiomarkers so that the position of the electrodes of the electrode assembly can be detected.

In certain embodiments, the electrodes are spaced approximately 2.5 centimeters apart. Preferably, the electrodes are spaced such that there is one or more electrodes adjacent to each nerve bundle so that an electromagnetic field is applied to nerves above and below the site that may be damaged. In certain embodiments, the lead diameter is up to the diameter of chest tubes (about 16 F to about 24 F for children and about 36 F for adults). Thus, the lead diameter can be larger than the diameter of standard neurostimulation leads (e.g. about 8 to about 12 mm versus about 1.3 mm for neurostimulation leads). In certain embodiments, the electrodes are about 2 mm to about 5 mm in length.

The electrodes can be inserted into the pleural space at the end of a thoracic surgical procedure where the electrodes can be directly positioned over the interocostal nerve bundles under direct visualization. Similarly, the electrode can be tunneled under the skin and be on the outside of the rib cage adjacent to the intercostal bundle. Alternatively and in addition, the electrodes can be placed directly on the skin overlying the intercostal bundle. The electrodes or plurality of electrodes can also be inserted next to abdominal muscle or fascia at the end of abdominal surgeries.

Figure 7:
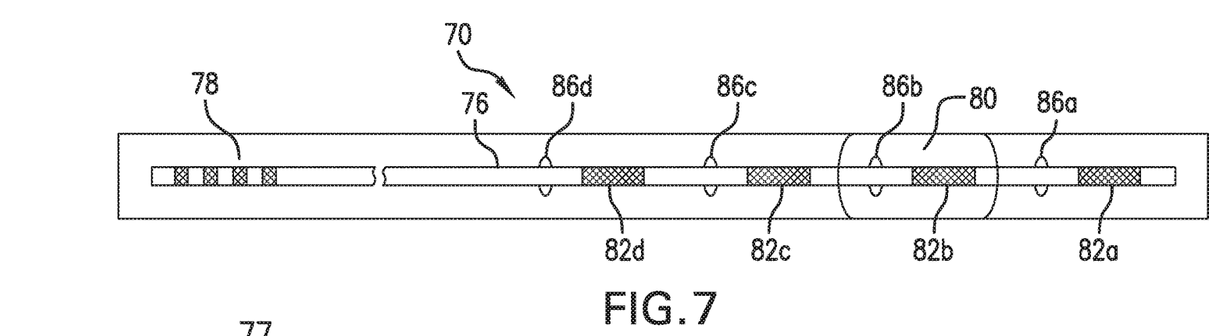
FIG. 7 is a top view of an electrical lead of an electrode assembly system according to an embodiment of the present disclosure.
Figure 8:
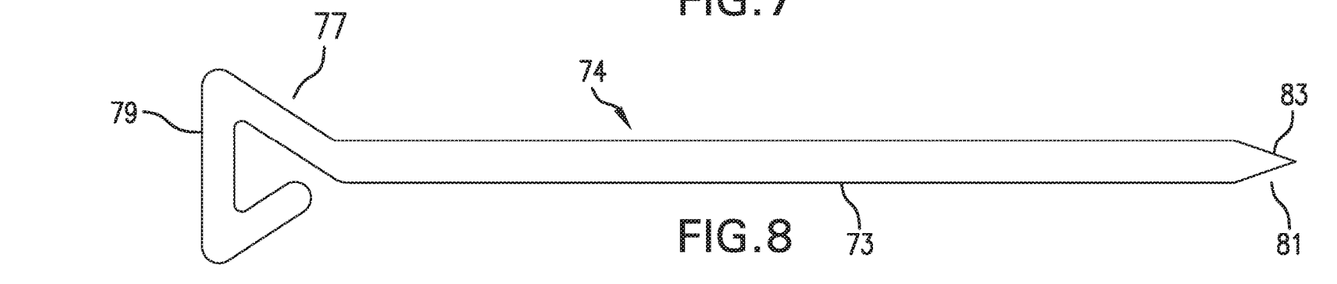
FIG. 8 is a top view of a tunneler of an electrode assembly system according to an embodiment of the present disclosure.
Figure 9:
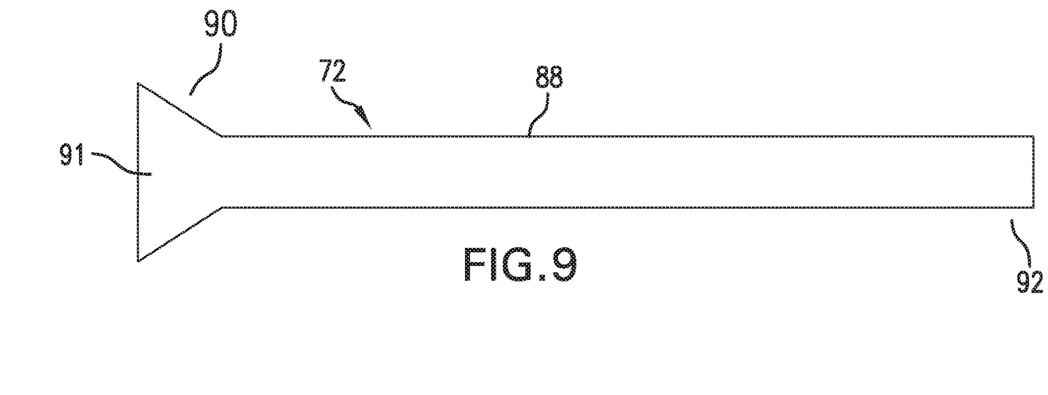
FIG. 9 is a top view of a sheath of an electrode assembly system according to an embodiment of the disclosure.
Figure 10:
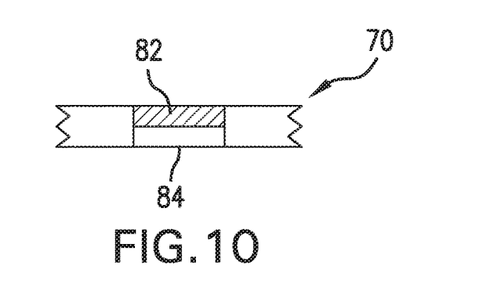
FIG. 10 is a side view of an electrical lead according to an embodiment of the present disclosure.

Referring to FIGS. 7-9, certain embodiments provide for an electrode assembly system that can be placed subcutaneously over a plurality of intercostal nerve bundles. Such an electrode assembly system comprises an electrical lead 70, a sheath 72 and a tunneler 74. As illustrated in FIG. 7, electrical lead 70 comprises a lead body 76 having a proximal portion 78 and a distal portion 80. Although lead body 76 is illustrated as having a cylindrical configuration, the lead body can have a flat or paddle-like configuration, as depicted in FIG. 6 and FIG. 4, respectively. Distal portion 80 comprises a plurality of un-insulated electrically conductive sections 82 and a plurality of opposing insulated sections 84 as illustrated in FIG. 10. Electrical lead 70 can also comprise a plurality of flexible stabilizing tines 86 laterally extending from distal portion 80 of lead body 76. The stabilizing tines can have any suitable shape so long as they prevent the distal portion of the electrical lead from axially migrating or rotating. For example, the stabilizing tines can have a substantially triangular configuration. Further the stabilizing tines are fabricated from a material such as silicone or thermoplastic polyurethane, for example, to minimize tissue in-growth and to flex proximally as the electrical lead is removed from under the patient's skin.

Figure 11:
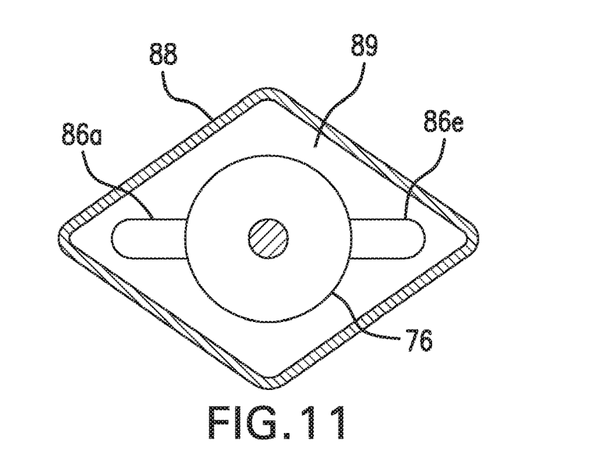
FIG. 11 is a cross-sectional view of a sheath with an electrical lead disposed therein according to an embodiment of an electrode assembly system of the present disclosure.
Figure 12:
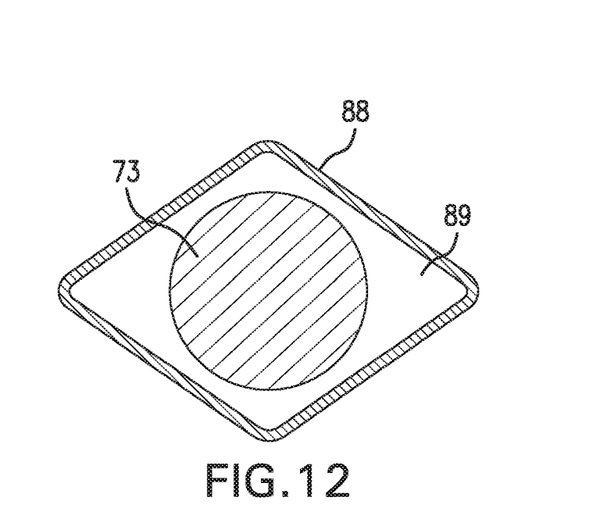
FIG. 12 is a cross-sectional view of a sheath with a tunneler disposed therein according to an embodiment of an electrode assembly system of the present disclosure.

As illustrated in FIGS. 9, 11 and 12, sheath 72 comprises a sheath body 88 having a proximal end 90, a distal end 92, and a lumen 89 extending therebetween. Sheath 72 can be peeled away in sheets. In such embodiments, sheath can comprise a plastic material. In certain embodiments, proximal end 90 includes an alignment fin 91, described in more detail below, which has width greater than distal end 92 of sheath body 88. Lumen 89 of sheath body 88 is sized to accommodate both lead body 76 of electrical lead 70 and tunneler body 73 of tunneler 74 as illustrated in FIGS. 11 and 12. FIG. 11 is a cross-sectional view of sheath body 88 of sheath 72 with electrical lead body 76 disposed within lumen 89. As can be seen from this figure, sheath body 88 has a cross-sectional configuration that accommodates the plurality of stabilizing tines 86.

Referring to FIG. 8, tunneler 74 comprises a tunneler body 73 having a proximal end 77 and a distal end 81. Proximal end 77 preferably comprises an alignment handle 79, described in more detail below, which has a width greater than the distal end 92 of tunneler body 73. Distal end 81 preferably has a tapered or pointed tip 83 such that tunneler body 73 can be inserted under a patient's skin to create a pathway for subcutaneous insertion of portions of sheath 72 and electrical lead 70, as described in more detail below. The tunneler can be malleable so that an operator can curve the tunneler to match the contour of the patient's chest. As illustrated in FIG. 12, which is a cross-sectional view of sheath body 88 with tunneler body 73 disposed within lumen 89, sheath body 88 also has a cross-sectional configuration that accommodates at least a portion of tunneler 74.

Figure 13:
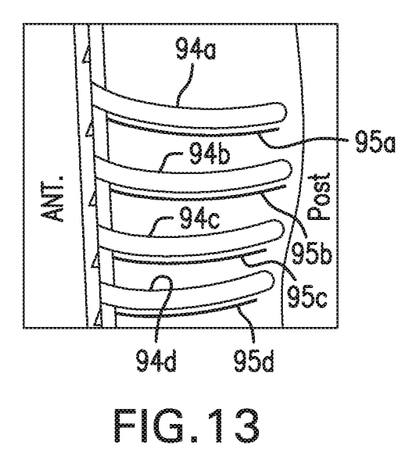
FIG. 13 is a schematic illustration of a patient's thoracic cavity illustrating a patient's ribs and a plurality of intercostal nerve bundles.
Figure 14:
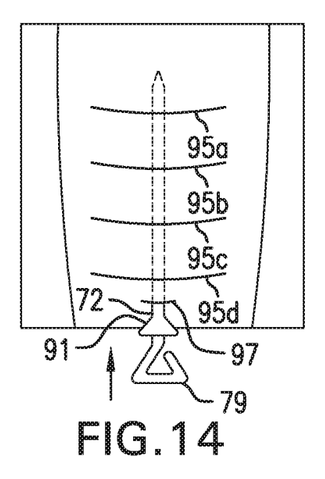
FIG. 14 is a schematic illustration of a patient's thoracic cavity illustrating a sheath with a tunneler disposed therein inserted under the patient's skin over the patient's intercostal nerve bundles according to an embodiment of the present disclosure.
Figure 15:
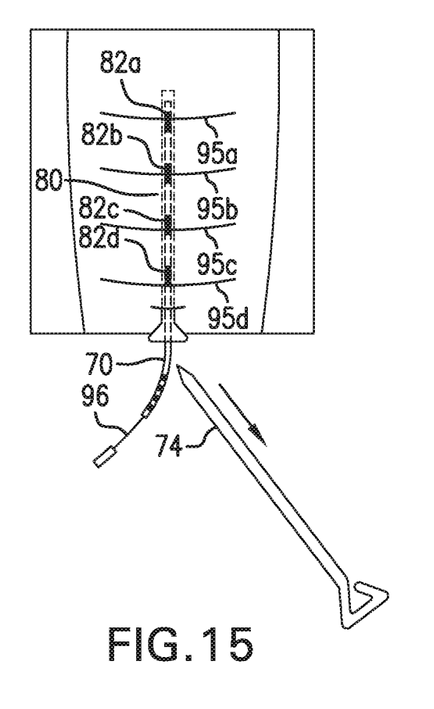
FIG. 15 is a schematic illustration of a patient's thoracic cavity illustrating the tunneler of FIG. 14 removed from under the patient's skin and an electrical lead inserted into the sheath of FIG. 14.
Figure 16:
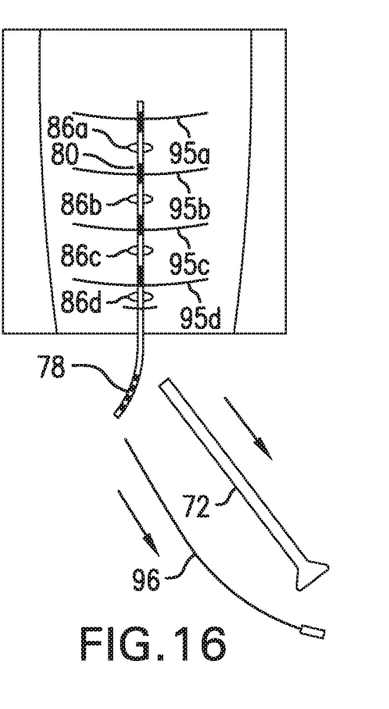
FIG. 16 is a schematic illustration of a patient's thoracic cavity with the sheath of FIG. 15 removed from under the patient's skin and the electrical lead of FIG. 15 stabilized over the patient's intercostal nerve bundles.

With reference to FIGS. 13-16, the present disclosure also provides a method of using the electrode assembly system depicted in FIGS. 7-9. FIGS. 13-16 are schematic illustrations of a lateral view of a patient's intercostal nerve bundles. FIG. 13 illustrates the patient's ribs 94 and a plurality of intercostal nerve bundles 95. FIGS. 14-16 only illustrate the patient's intercostal nerve bundles 95 for the sake of clarity. Referring to FIG. 14, sheath 72 with tunneler 74 disposed therein is placed through an incision 97 in the patient's skin in the appropriate subcutaneous plane such that sheath 72 is positioned over the plurality of intercostal nerve bundles 95. Alignment fin 91 and alignment handle 79 remain outside the patient's skin substantially perpendicular to the patient's ribs 94 and/or the incision site 97. In alternative embodiments, the alignment fin and alignment handle remain outside the patient's skin substantially parallel to the patient's ribs and/or incision site. Referring to FIG. 15, tunneler 74 is withdrawn from sheath 72 and sheath 72 remains in place over the plurality of intercostal nerve bundles 95. Alignment fin 91 remains substantially perpendicular to the patient's ribs 94 and/or the incision site 97. Distal portion 80 of electrical lead 70 with a pre-loaded stylet 96 disposed therein is inserted into sheath 72. Stabilizing tines 86 are not depicted in FIG. 15 for the sake of clarity. Distal portion 80 of electrical lead 70 is oriented such that the un-insulated electrically conductive sections 82 are facing toward the plurality of intercostal nerve bundles 95 and the plurality of opposing insulated sections (not shown for purposes of clarity) are facing towards the patient's cutaneous fibers. Fluoroscopy can be used to position the electrically conductive sections 82 over the plurality of intercostal nerve bundles 95 based on the position of the electrically conductive sections 82 relative to the patient's ribs 94. Referring to FIG. 16, stylet 96 is held in place allowing sheath 72 to be removed with distal portion 80 of electrical lead 70 remaining in place in the desired position over the plurality of intercostal nerve bundles 95. Sheath 72 can be a solid tube or can be a peel-away tube if necessary for removal over other system components. Stylet 96 is then removed. As seen in FIG. 16, proximal portion 78 of electrical lead 70 is exposed and not under the patient's skin. Proximal portion 78 is then connected to a pulse generator (not shown for purposes of clarity) and an electromagnetic field is applied to the plurality of intercostal nerve bundles 95. Distal portion 80 of electrical lead 70 is withdrawn axially (not shown for purposes of clarity) after achieving an intercostal nerve block sufficient to alleviate the patient's pain. Since stabilizing tines 86 are fabricated from a flexible material, they bend in a proximal direction as distal portion 80 of electrical lead 70 is removed from under the patient's skin.

Figure 2:
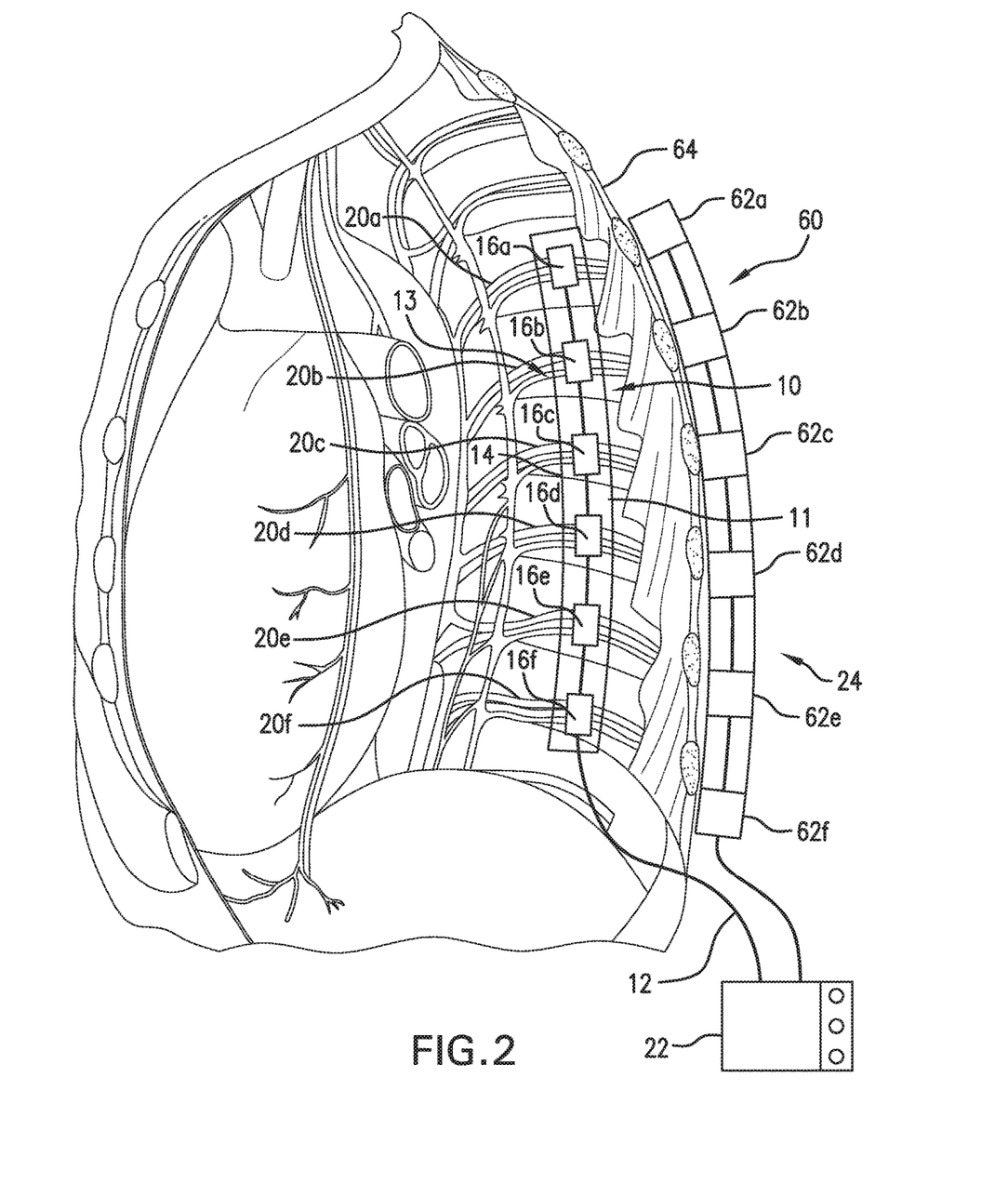
FIG. 2 is a schematic illustration of a thoracic cavity with embodiments of electrode assemblies positioned over a plurality of intercostal nerve bundles.

Referring back to FIG. 2, in certain embodiments, a second electrical lead 60 comprising a plurality of electrodes 62 can be placed on the outside surface of the patient's chest wall 64. Second electrical lead 60 can also be connected to pulse generator 22 (or a separate pulse generator) to apply an electromagnetic field to intercostal nerve bundles 20. Such an embodiment results in application of an electromagnetic field on both sides of intercostal nerve bundles 20. Although an electrical lead is depicted in FIG. 2, other configurations of an electrode assembly can be placed on the outside of the patient's chest wall.

Although FIGS. 2-5 illustrate an electrode assembly placed in a patient's chest, the electrode assembly can be placed in other locations over the plurality of intercostal nerve bundles so long as an electromagnetic field can be applied to the plurality of intercostal nerve bundles to achieve a nerve block sufficient to alleviate the patient's pain. For example, the electrode assembly can be placed under the skin overlying the ribs or placed on the skin overlying the intercostal nerve bundles. As such, the electrode assembly can be placed over the intercostal nerve bundles at the end of the surgery but before the chest or abdominal cavity is closed (if involving an open surgery), subcutaneously after the surgery, or transcutaneously after the surgery. In certain embodiments, the surgery is open surgery including, for example, thoracic, cardiac, or abdominal surgery. In other embodiments, the surgery is for treating a traumatic injury such as a multiple rib fractures, for example.

The electromagnetic field is applied to the plurality of intercostal nerve bundles after surgery, meaning the immediate time period post-operative after recovery from anesthesia. High frequency stimulation can be applied to achieve a sufficient nerve block. Certain exemplary stimulus parameters are applicable to the therapy, including a current amplitude between about 0 to about 30 mA; a pulse width between about 10 to about 500 microseconds; a frequency between about 2 Hz to about 50 kHz. The waveform can be charge-balanced, biphasic with sinusoidal, square wave or asymmetric pulse type. As mentioned above, an electromagnetic field is applied to the plurality of intercostal nerve fibers to achieve a nerve block sufficient to alleviate the patient's pain. In certain instances, the electrical lead remains in place over the patient's intercostal nerve bundles for a minimum of 3-5 days post-operatively.

Methods and devices of the present disclosure can provide pain control after thoracic and non-thoracic surgeries and thereby significantly improve the patient's post-operative recovery. Such methods and devices of pain control may avoid or decrease the administration of narcotics and other traditional pharmacologic agents and therefore eliminate the side effects of systemic medications. Such methods and devices also eliminate the need for invasive epidural/spinal/paravertebral catheter placement as mentioned above.

Although methods and systems of the present disclosure have been described primarily with respect to reducing post-operative pain, methods and systems as generally described herein can have other applications include managing chronic thoracic nerve pain. For example, methods and systems can be used After Video Assisted Thoracic Surgery (VATS), robotic assisted cardiac surgery, robotic assisted cardiac valve surgery, open thoracic surgery and/or abdominal surgery, minimally invasive thoracic surgery and/or abdominal surgery.

Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures. For example, although certain figures illustrate electrodes, electrical contacts or electrical nodes positioned substantially perpendicular to the intercostal nerve bundles or ribs, the electrodes, electrical contacts or electrical nodes can be positioned substantially parallel to the intercostals nerve bundles or ribs. Additionally, when describing a range, all points within that range are included in this disclosure. In addition, unless otherwise specified, none of the steps of the methods of the present disclosure are confined to any particular order of performance. Furthermore, all references cited herein are incorporated by reference in their entirety.

What is claimed is:

1. A method of providing an intercostal nerve block to a patient experiencing pain in the abdominal or thoracic region after surgery in the abdominal or thoracic region, the method comprising:
    obtaining an electrode assembly having a proximal portion and a distal portion, the distal portion comprising a plurality of electrodes;
    placing in the abdominal or thoracic region where the patient is experiencing pain an electrode of the plurality of electrodes over each of a plurality of intercostal nerves of the patient's body;
    connecting the proximal portion of the electrode assembly to a pulse generator; applying in the abdominal or thoracic region where the patient is experiencing pain an electromagnetic field to each of the plurality of intercostal nerves after the patient's surgery;
    percutaneously removing the distal portion of the electrode assembly from the patient's body after achieving an intercostal nerve block; and thereby
    alleviating the patient's pain in the abdominal or thoracic region where the patient is experiencing pain after achieving the intercostal nerve block.

2. The method of claim 1, wherein the distal portion further comprises a plurality of insulated sections opposing the plurality of electrodes.

3. The method of claim 1, further comprising retracting the proximal portion of the electrode assembly from the patient's body prior to connecting the proximal portion to the pulse generator.

4. The method of claim 2, further comprising positioning the distal portion of the electrode assembly in the patient's body such that the plurality of electrodes faces the plurality of intercostal nerves and the plurality of insulated sections faces cutaneous fibers of the patient's body such that the electromagnetic field is directed towards the plurality of intercostal nerves and away from the cutaneous fibers.

5. The method of claim 1, further comprising:
    obtaining another electrode assembly having a proximal portion and a distal portion, the distal portion comprising a plurality of electrodes;
    placing the distal portion of the another electrode assembly on the outside surface of the patient's chest wall;
    connecting the proximal portion of the another electrode assembly to the pulse generator of claim 1 or another pulse generator; and
    applying another electromagnetic field to the plurality of intercostal nerves after the patient's surgery in order to apply electromagnetic fields to both sides of the plurality of intercostal nerves.

6. The method of claim 1, wherein the surgery is open surgery.

7. The method of claim 6, wherein the open surgery is thoracic surgery, cardiac surgery or abdominal surgery.

8. The method of claim 1, wherein the surgery for treating a traumatic injury.

9. The method of claim 8, wherein the traumatic injury is a rib fracture.

10. The method of claim 1, wherein the placing step comprises placing the plurality of electrodes in the patient's chest.

11. The method of claim 1, wherein the placing step comprises placing the plurality of electrodes under the patient's skin overlying the ribs.

12. The method of claim 1, wherein the electrode assembly is disposed on a paddle-style lead.

13. The method of claim 12, wherein the plurality of electrodes of the electrode assembly are cylindrical electrodes that are partially embedded in the paddle-style lead.

14. A method of providing an intercostal nerve block to a patient experiencing pain in the abdominal or thoracic region after surgery in the abdominal or thoracic region, the method comprising:
    obtaining an electrode assembly comprising a plurality of electrical nodes and an electrical wire electrically coupled to the plurality of electrical nodes;
    placing in the abdominal or thoracic region where the patient is experiencing pain an electrical node of the plurality of electrical nodes over each of a plurality of intercostal nerves of the patient's body;
    connecting the electrical wire to a pulse generator;

applying in the abdominal or thoracic region where the patient is experiencing pain an electromagnetic field to each of the plurality of intercostal nerves after the surgery;

percutaneously removing the distal portion of the electrode assembly from the patient's body after achieving an intercostal nerve block; and thereby alleviating the patient's pain in the abdominal or thoracic region where the patient is experiencing pain after achieving the intercostal nerve block.

15. A method of providing an intercostal nerve block to a patient experiencing pain in the abdominal or thoracic region after surgery in the abdominal or thoracic region, the method comprising:

obtaining an electrical lead comprising a lead body having a proximal portion and a distal portion, the distal portion comprising a plurality of electrodes;

placing in the abdominal or thoracic region where the patient is experiencing pain an electrode of the plurality of electrodes over each of a plurality of intercostal nerves of the patient's body;

connecting the proximal portion of the lead to a pulse generator;

applying in the abdominal or thoracic region where the patient is experiencing pain an electromagnetic field to each of the plurality of intercostal nerves after the surgery;

percutaneously removing the distal portion of the electrode assembly from the patient's body after achieving an intercostal nerve block; and thereby alleviating the patient's pain in the abdominal or thoracic region where the patient is experiencing pain after achieving the intercostal nerve block.

16. A method of providing an intercostal nerve block to a patient experiencing pain in the abdominal or thoracic region after surgery in the abdominal or thoracic region, the method comprising:

obtaining an electrode assembly system comprising:
an electrical lead comprising:
a lead body having a proximal portion and a distal portion, the distal portion comprising a plurality of un-insulated electrically conductive sections and a plurality of opposing insulated sections;
a plurality of flexible stabilizing tines laterally extending from the distal portion of the lead body
a sheath comprising:
a sheath body having a proximal end, a distal end, and a lumen extending therebetween, the sheath body having a cross-sectional configuration that accommodates the plurality of stabilizing tines; and
a tunneler comprising a tunneler body having a proximal end and a distal end, at least a portion of the tunneler configured to be disposed within the sheath;

inserting through an incision site in the patient's skin the sheath with the tunneler disposed therein;

positioning the sheath subcutaneously over a plurality of intercostal nerves;

withdrawing the tunneler;

inserting the distal portion of the electrical lead into the sheath;

orienting the distal portion of the electrical lead such that the plurality of un-insulated electrically conductive sections are facing towards the plurality of intercostal nerves in the abdominal or thoracic region where the patient is experiencing pain and away from cutaneous fibers of the patient's body;

removing the sheath;

connecting the proximal portion of the electrical lead to a pulse generator;

applying in the abdominal or thoracic region where the patient is experiencing pain an electromagnetic field to the plurality of intercostal nerves;

withdrawing the distal portion of the electrical lead after achieving an intercostal nerve block; and thereby alleviating the patient's pain in the abdominal or thoracic region where the patient is experiencing pain after achieving the intercostal nerve block.

17. The method of claim 16, wherein the opposing insulated sections are facing towards the cutaneous fibers.

18. The method of claim 16, wherein:
the proximal end of the sheath body comprises an alignment fin having a width greater than the distal end of the sheath body; and
the proximal end of the tunneler body comprises an alignment handle having a width greater than the distal end of the tunneler body.

19. The method of claim 18, wherein the alignment fin and the alignment handle are positioned outside of the patient's skin substantially perpendicular to the patient's ribs and/or the incision site.

* * * * *